United States Patent [19]

Panzera et al.

[11] Patent Number: 5,314,334
[45] Date of Patent: * May 24, 1994

[54] DENTAL PROCELAIN BOND LAYER FOR TITANIUM AND TITANIUM ALLOY COPINGS

[75] Inventors: Carlino Panzera, Belle Mead, N.J.; Arun Prasad, Cheshire, Conn.

[73] Assignee: American Thermocraft Corporation Subsidiary of Jeneric/Pentron Incorporated, Somerset, N.J.

[ * ] Notice: The portion of the term of this patent subsequent to Jun. 6, 2008 has been disclaimed.

[21] Appl. No.: 711,066

[22] Filed: Jun. 6, 1991

Related U.S. Application Data

[63] Continuation-in-part of Ser. No. 629,617, Dec. 18, 1990, abandoned.

[51] Int. Cl.$^5$ .............................................. A61C 13/08
[52] U.S. Cl. ..................... 433/206; 428/212; 428/432; 428/469; 428/472; 428/697; 428/701; 428/702; 433/202.1; 433/212.1; 433/222.1
[58] Field of Search ............... 428/469, 472, 434, 212, 428/697, 701, 702, 432; 433/212.1, 222.1, 206, 202.1; 501/65, 66, 67

[56] References Cited

U.S. PATENT DOCUMENTS

| | | | |
|---|---|---|---|
| 4,104,798 | 8/1978 | Takahi et al. | 433/222.1 |
| 4,159,358 | 6/1979 | Hench et al. | 428/434 |
| 4,215,033 | 7/1980 | Bowen | 433/222 |
| 4,671,770 | 6/1987 | Bell et al. | 433/222.1 |
| 4,684,555 | 8/1987 | Neumeyer | 428/469 |

FOREIGN PATENT DOCUMENTS 0183335 11/1982 Japan .

*Primary Examiner*—A. A. Turner
*Attorney, Agent, or Firm*—Watson, Cole, Grindle & Watson

[57] ABSTRACT

Porcelain compositions suitable for layers on metal base dental restorations have fusion temperatures of about 800° C. and lower. The compositions may be employed as coatings on titanium and titanium alloy bases since the compositions have thermal expansion values close to those of titanium and its alloys. A bond layer is also provided to improve bonding between the porcelain layers and the restoration base. A method is also provided for forming dental restorations with relatively inexpensive and biocompatible metal bases and low fusing dental porcelains.

9 Claims, No Drawings

DENTAL PROCELAIN BOND LAYER FOR TITANIUM AND TITANIUM ALLOY COPINGS

RELATED APPLICATION

This application is a continuation-in-part of U.S. Ser. No. 07/629,617 filed Dec. 18, 1990 now abandoned.

FIELD OF THE INVENTION

This invention relates to dental porcelains having thermal expansion values near that of titanium. More particularly, the present invention relates to dental porcelains which have a low fusion temperature and which fluoresce like natural dentition. The present invention further relates to dental restorations and bond layers for such restorations.

BACKGROUND OF THE INVENTION

Dental crown and bridge restorations are often made with a metal base having a jacket or covering of dental porcelain so that the restoration will closely resemble a natural tooth. Such restorations are well known and have been used for many years.

The general technique for the construction of a porcelain coated dental restoration (i.e. crown or bridge), involves first taking an impression of a denture area that has been prepared to receive the restoration. A die is prepared from the impression and a metal base ("coping") is cast to fit this die. The metal base has an internal shape to match the prepared denture. A porcelain powder is then mixed with water to form a slurry which is then applied to the metal base by standard procedures. The slurry is shaped in the form of the finished crown or multiple unit bridge. The porcelain is then dried, and fired in a furnace at a desired firing temperature. The crown or bridge may be fired several times before the final form is obtained, and the porcelain may be applied in several layers.

There is a significant temperature change from the firing temperature to room temperature, as a restoration is alternately cooled and fired. Therefore, significant stress can be induced in the restoration if the thermal expansion of the porcelain coating does not closely match that of the metal base.

Metal bases that are most often employed today in such restorations include gold, high and low gold alloys including gold-palladium alloys, silver-palladium alloys, high palladium alloys, nickel-chrome-molybdenum type alloys, gold-silver-palladium alloys and palladium-copper alloys. Gold and its alloys are preferred metals for a metal base due to their biocompatibility with the human body. Gold, however, is a very expensive metal and, like other metals typically used for dental restorations, it requires high fusing temperatures to bond with a jacket or covering of dental porcelain. These metals and alloys exhibit thermal expansion coefficients of about $14 \times 10^{-6}$ in/in/°C. and thus ceramics used in combination therewith have similarly high thermal expansion coefficients.

Current commercially available dental porcelains have fusion temperatures in the range of 1700° F. and up. High fusion temperatures of today's dental porcelains prevent their use with certain metals which readily oxidize at high temperatures.

It is therefore desirable to provide a dental restoration which comprises a metal base, or coping, which is biocompatible with the human body and which is not very expensive. It is also desirable to provide a dental porcelain which may be used with an inexpensive, biocompatible metal having a low thermal expansion. The present invention also relates to a dental porcelain which has a low fusing temperature and which bonds securely to a metal base.

SUMMARY OF THE INVENTION

The present invention provides a dental restoration which has a metal base made of titanium or a titanium alloy. The restorations of the present invention also comprise porcelain materials which have thermal expansion coefficients close to that of titanium and fusion temperatures of less than 800° C. The porcelains of the present invention tend to absorb oxygen while fusing which advantageously reduces the amount of titanium oxidation during fusing. The porcelains of the present invention also provide a variable degree of fluorescence so as to closely resemble natural dentition. The present invention also provides a method for preparing dental restorations.

Yet another aspect of the present invention relates to a method of making a dental restoration wherein a titanium or titanium alloy metal base is coated with a dental porcelain and heated to a fusing temperature of less than 800° C. In one embodiment, a bond layer is provided which improves the adhesion of the porcelain to the base. The bond layer is particularly important when alloy impurities are present in an alloy base, and under certain casting conditions when making a coping. Also, under some conditions of porcelain fusion when making a crown or bridge the porcelain does not properly bond, thus necessitating a bond layer.

DETAILED DESCRIPTION OF THE INVENTION

According to an embodiment of the present invention, titanium or a titanium alloy is used as the metal base for a dental restoration. Titanium and most of its alloys are extremely biocompatible, and provide the strength and longevity necessary for dental restorations. Unlike precious metals such as gold, titanium and its alloys are relatively inexpensive. Current, commercially available dental porcelains are not compatible with titanium or its alloys because thermal expansion and fusion temperatures of these porcelains are too high.

The present invention also provides a dental porcelain which has a thermal expansion coefficient close to that of titanium (approximately $9.91 \times 10^{-6}$ in/in/°C. room temperature to 570° C.) and a fusion temperature of less than 850° C., preferably less than 800° C. When heated to more than 800° C., titanium readily oxidizes and also transforms from an alpha crystalline structure to a beta crystalline structure which may induce harmful stresses. Therefore, when using a titanium metal base, it is desired to employ a dental porcelain having a fusion temperature of less than 800° C. (approximately 1470° F). The present invention also provides a dental porcelain which absorbs oxygen rather than produces oxygen to even further minimize the amount of oxidation of the titanium.

The present invention also provides a special bond layer which is applied to the restoration base prior to application of the dental porcelain. The bond layer is especially useful for bases comprising titanium or titanium alloys, however, the bond layer may also be applicable to other types of restoration bases.

Of the titanium alloys useful in accordance with the present invention titanium 6.4 is a preferred alloy. Titanium 6.4 comprises 6 percent aluminum, 4 percent vanadium and the remainder is titanium. Other titanium alloys may be used provided they have low thermal expansion coefficients. Another preferred alloy comprises 5 percent aluminum and 2.5 percent tin.

Preferred dental porcelains according to the present invention preferably comprise oxides of silicon, boron, sodium, potassium, cerium, zinc, titanium, zirconium, tin, barium, lithium, calcium and magnesium. Fluorides of alkali and alkaline earth metals may be substituted for or used in combination with all or some of the oxides listed above. In particular, calcium magnesium, and strontium fluorides may be used. Various combinations of these oxides may be employed according to the present invention provided they form porcelains having a thermal expansion coefficient close to that of titanium and a fusion temperature of less than 800° C.

Silicon dioxide is a major component of porcelains according to the present invention. Silicon dioxide has a fusion temperature of approximately 1700° C., much too high to be compatible with titanium independently. According to the present invention, porcelains comprising greater than about 50 percent silicon dioxide are preferred. Porcelains having silicon dioxide present in an amount of between about 58 and about 65 percent by weight are more preferred, while those having about 61 percent are most preferred.

Aluminum oxide may also be used in porcelains according to the present invention, however, it is not necessary. If used, amounts between about one and about four percent by weight are preferred, about two percent being most preferred.

In order to reduce the fusion temperature of the porcelains of the present invention, boron oxide ($B_2O_3$) and sodium oxide ($Na_2O$) may be added to the porcelain mixtures. Boron oxide is also used to increase the durability of a dental porcelain. Preferably, boron oxide is present in an amount of between about seven and about 13 percent by weight of the porcelain mixture although amounts of up to 30 percent may be used. Most preferably, boron oxide is present in an amount of about nine percent by weight. Sodium oxide is preferably present in an amount of up to about 12 percent by weight, most preferably, about eight percent. If no sodium oxide is used, the weight percent of boron oxide, potassium oxide or both may be increased. Potassium oxide may be substituted for sodium oxide or both may be used.

According to the present invention, potassium oxide ($K_2O$) may be used and is preferably present in an amount of up to about eight percent by weight. Preferably, potassium oxide is present in an amount of about six percent by weight. If no potassium oxide is used, the weight percent of boron oxide, sodium oxide, or both may be increased.

To increase the bonding strength of porcelains according to the present invention, cerium oxide and zinc oxide may be added to the porcelain mixtures prior to dissolving. Only a small amount of cerium oxide is necessary to greatly improve bonding between about one and about three percent by weight, two percent being more preferred. Zinc oxide is preferably present in greater amounts such as about eight to about eleven percent by weight. About nine percent by weight zinc oxide is most preferred.

Titanium oxide is also useful in porcelains according to the present invention. The amount of titanium oxide preferred is between about two and about four percent by weight, three percent being most preferred.

Zirconium oxide and a complex of yttrium oxide and cerium oxide are optional ingredients. If used, the zirconium oxide is present in an amount of up to about one percent by weight, preferably about 0.5 percent by weight. Zirconium oxide is primarily used as an opacifier for the porcelain. The yttrium oxide-cerium oxide complex may be used to add fluorescence to the porcelains. If used, amounts of up to only about one percent by weight are necessary to provide dentition having natural-looking fluorescence. About 0.3 percent by weight of the complex is most preferred.

The above mixtures make up body porcelains which may be used in combination with a titanium or titanium alloy base. Preferred body porcelain materials of the present invention have the following compositions:

| COMPONENT | WEIGHT PERCENT | |
|---|---|---|
| | BROAD | PREFERRED |
| $SiO_2$ | 50–70 | 58–65 |
| $Al_2O_3$ | 0–4 | 1–4 |
| $B_2O_3$ | 7–33 | 7–13 |
| $Na_2O$ | 0–20 | 6–12 |
| $K_2O$ | 0–20 | 5–8 |
| $CeO_2$ | 0–3 | 1–3 |
| ZnO | 0–11 | 8–11 |
| $TiO_2$ | 0–4 | 2–4 |
| $ZrO_2$ | 0–1 | 0–1 |
| $Y_2O_3$—$Ce_2O_3$ | 0–1 | 0–1 |
| BaO | 0–15 | 0–12 |
| $CaF_2$ | 0–5 | 0–4 |
| $Li_2O$ | 0–5 | 0–3 |
| CaO | 0–5 | 0–3 |

The body porcelain may be formed by mixing the various oxides together with the exception of the opacifier and fluorescing agent which are added later. The mixture of various oxides is then heated until all the oxides melt and dissolve. This temperature may exceed 1500° C. for some combinations of the oxides. Once the oxides melt and fuse together, a uniform clear molten mass is produced. The mass is then cooled to form a clear glass which has a randomly oriented atomic structure and little, if any, crystalline arrangement. The glass is then crushed to form a powder having an average particle size of up to about 70 microns. Preferably, the particles have an average size of between about 15 and about 20 microns. The opacifier and fluorescing agents may then be added if desired. The powder may then be wetted and applied in the form of a paste to a metal base or an opaque ceramic and heated to about 800° C. where it fuses to form a dental restoration. Temperatures as low as about 780° C. may be used to fuse the body porcelain. Typically, the body porcelain is applied to a layer of opaque porcelain which has been painted onto a metal base. The body porcelain may be used by itself, however, greater amounts of pigments would need to be added to the body porcelain so as to disguise the metal base.

In order to improve the bonding between the metal and the porcelain, an opaque porcelain is preferably prepared and used to prime the metal base for bonding with the body porcelain. The opaque porcelain comprises approximately 70 to 80 percent by weight body porcelain. Most preferably, the opaque porcelain comprises about 75 percent by weight body porcelain. The remainder of the opaque porcelain comprises at least one member selected from the group consisting of titanium oxide, cerium oxide, stannic oxide and zinc oxide. Most preferably, all 4 oxides are combined to make up the remaining 20 to 30 percent by weight of the opaque porcelain. When all four oxides are used, the titanium oxide is preferably present in an amount of between about four and about six percent by weight, most preferably about five percent by weight. The cerium oxide is preferably present in an amount of between about four and about six percent by weight, most preferably about five percent by weight. The stannic oxide is preferably present in an amount of between about eight and about 12 percent by weight, most preferably, about 10 percent by weight. The zinc oxide is preferably present in an amount of between about four and about six percent by weight, most preferably, about five percent by weight. In a preferred embodiment, the opaque porcelain comprises seventy-five percent by weight body porcelain and twenty-five percent by weight a mixture of titanium oxide, cerium oxide, stannic oxide and zinc oxide. These 4 oxides are pulverized and mixed with powdered body porcelain and then fused to form the opaque porcelain. When the opaque porcelain is fused to the metal base prior to fusing the body porcelain to the metal base, fusing of the body porcelain to the base is greatly improved. After coating the metal with the opaque porcelain, the body porcelain is then coated on the opaque porcelain and the entire structure is heated to near 800° C.

Preferred opaque porcelain materials of the present invention have the following compositions:

| COMPONENT | WEIGHT PERCENT | | |
|---|---|---|---|
| | BROAD | PREFERRED | MORE PREFERRED |
| Body Porcelain | 70–80 | 70–80 | 75 |
| $TiO_2$ | 0–30 | 4–6 | 5 |
| $CeO_2$ | 0–30 | 4–6 | 5 |
| $SnO_2$ | 0–30 | 8–12 | 10 |
| ZnO | 0–30 | 4–6 | 5 |

To form the opaque porcelain, about 70 to 80 percent by weight of the body porcelain in a powdered form is mixed with about 20–30 percent by weight of a mixture of the four oxides mentioned above with respect to the opaque porcelain. This new mixture is then heated to about 1000° C., below the melting point of the oxides. At this temperature, the body porcelain glass fuses with the oxide particles to form a hard mass which is opaque. The hard mass is then crushed to form opaque porcelain particles of about the same size as desired for the body porcelain or finer. Particle sizes of about 15 to 20 microns are preferred. The opaque may be applied to a metal base and fused at temperatures as low as about 800° C.

When applying the opaque porcelain to the metal base, the porcelain is typically first mixed with a liquid vehicle so that it may be applied to the base. The liquid vehicle may comprise water, organic solvents, or other liquid carriers which are inert to the reaction between the porcelain and the titanium. One preferred liquid vehicle is Smooth Touch ™ (available from Jeneric/Pentron, Wallingford, Conn.) which comprises water with wetting agents. Upon heating to fusion temperatures, the liquid typically evaporates and is preferably completely removed from the system.

When dental restorations according to the present invention are formed in a furnace, it is preferable to provide a vacuum in the furnace so as to minimize the presence of oxygen. If present, oxygen will oxidize the titanium, particularly on exposed surfaces, which may weaken the bond between the titanium and the porcelain. Nitrogen in the air also reacts with titanium to form titanium nitride. Under vacuum conditions, the amount of nitrogen which can react with titanium may also be minimized. The use of a vacuum in a furnace also decreases the amount of bubbles formed in the porcelain. The dental restorations and porcelains of the present invention may be fired in conventional dental furnaces under much lower temperatures then generally needed for current, commercially available porcelains.

Oxidation of the titanium may also be minimized if the titanium metal base is completely covered with the porcelain upon application of the porcelain to the base. This reduces the amount of titanium surface area available on which oxygen can react. Also, porcelains according to the present invention tend to absorb oxygen and/or shield the alloy from nitrogen or oxygen which further decreases the amount of titanium oxidation and nitride formation.

Pigments may be added to the body porcelain and/or the opaque porcelain to form naturally looking restorations of various shades. These pigments are commercially available and well known to those of skill in the art.

To better improve adhesion of the body porcelain to the base, two layers of opaque porcelain can be applied, or, a bond layer and one layer of opaque. The bond layer, like the opaque and body porcelain, preferably comprises titanium dioxide and various glass forming metal oxides. Various alkali and alkaline earth metal fluorides may also be used in the bond layer. The bond layer promotes bonding of the opaque porcelain to restoration bases made of various alloys under diverse casting and porcelain fusion conditions. The glass formers of the bond layer preferably comprise at least one of boron oxide, silicon dioxide, sodium oxide and potassium oxide in powdered form. The glass formers are blended with titanium dioxide and other metal oxides, and heated to about 2000° F. for about 2 hours until the blend melts. The metal oxides can be added as individual components or as a part of a metal. For example, kaolin may be used to provide $Al_2O_3$ and $SiO_2$. The melted blend is cooled slowly to a solid mass (boule) which is subsequently pulverized to a powder.

The glass formers and metal oxides initially mixed preferably have average particle sizes of between 0.5 and 70 microns in diameter. More preferably, the particles have an average size of between about 15 and about 20 microns in diameter. After the various oxides are reacted to form the solid mass, they are preferably pulverized to form a powder which has an average particle size of up to about 70 microns in diameter. Preferably, the final powder has an average particle size of between about 15 and 20 microns in diameter.

Preferred bond layer porcelain materials of the present invention have the following compositions:

| COMPONENT | WEIGHT PERCENT | |
|---|---|---|
| | BROAD RANGE | PREFERRED RANGE |
| $TiO_2$ | 10–75 | 40–50 |
| $B_2O_3$ | 0–20 | 8–16 |
| $SiO_2$ | 0–20 | 8–14 |
| $Na_2O$ | 0–9 | 4–7 |
| $SnO_2$ | 0–10 | 4–8 |
| ZnO | 0–10 | 2–5 |
| $K_2O$ | 0–10 | 4–7 |

-continued

| COMPONENT | WEIGHT PERCENT BROAD RANGE | PREFERRED RANGE |
|---|---|---|
| $Al_2O_3$ | 0–15 | 4–10 |
| $Fe_2O_3$ | 0–5 | 2–4 |
| MgO | 0–4 | 1–3 |
| BaO | 0–15 | 0–12 |
| $CaF_2$ | 0–5 | 0–4 |
| $Li_2O$ | 0–5 | 0–3 |
| CaO | 0–5 | 0–3 |
| $CeO_2$ | 0–40 | 0–30 |

The powder porcelain for the bond layer is preferably mixed with a liquid vehicle prior to application to a restoration base or coping. The liquid vehicle may comprise water, organic solvents, or other liquid carriers which are preferably inert to the reaction between porcelain and titanium. One particularly useful liquid vehicle is Tyspar ™, available from Jeneric/Pentron, Inc., Wallingford, Conn. Another preferred liquid vehicle is Smooth Touch ™ (also available from Jeneric/Pentron, Inc.) which comprises water with wetting agents. After mixing with the liquid vehicle, a paste-like composition is formed which is then applied to the restoration base or coping and fired.

Good results are obtained when the bond layer coating is applied to the restoration base or coping and fired from about 600° F. to about 1470° F. at about 50° F./minute. More generally, starting temperatures from room temperature and below may be used. The ramping of this temperature enables outgasing of gases in the porcelain, preventing their entrapment. Trapped gases may cause weak spots and cause the opaque porcelain to become extremely white. Also, if immediately fired at a high temperature, the bond layer may explode from the build up of gases.

Firing is preferably performed under a vacuum pressure of about 26 to about 28 inches of mercury. Two particularly useful dental lab furnaces which have provided good results are the PF 120 ™ available from Jeneric/Pentron, Inc. and the Ney Sunfire 10 ™ available from Ney.

As with the opaque and body porcelains, the firing temperature for the bond layer should not exceed about 1470° F. to avoid oxidation of the titanium and conversion of the titanium to a beta crystalline structure. Temperatures slightly less than 1470° F. may be used, however, best results are obtained when heated to over 1400° F.

Although the methods and compositions in accordance with the present invention have been described in connection with preferred embodiments, it will be appreciated by those skilled in the art that additions, modifications, substitutions and deletions not specifically described may be made without departing from the spirit and scope of the invention defined in the appended claims.

We claim:

1. A dental restoration comprising a titanium or titanium alloy coping, a bond layer applied to said coping, and a body porcelain composition applied to said bond layer, wherein said bond layer comprises from about 10 to about 75 percent by weight titanium dioxide, from about 5 to about 20 percent by weight boron oxide and from about 5 to about 20 percent by weight silicon dioxide, and wherein said body porcelain composition comprising 50-70 percent by weight silicon dioxide and 7-33 percent by weight boron oxide.

2. A dental restoration as in claim 1, wherein said bond layer further comprises sodium oxide.

3. A dental restoration as in claim 1, wherein said bond layer further comprises at least one member selected from the group consisting of sodium oxide, stannic oxide, zinc oxide, potassium oxide, aluminum oxide, ferric oxide, magnesium oxide, barium oxide, lithium oxide, cerium oxide, calcium oxide and calcium fluoride.

4. A dental restoration as in claim 1, wherein said titanium dioxide is present in an amount of between about 40 and about 50 percent by weight.

5. A dental restoration as in claim 1, wherein said body porcelain further comprises at least one member selected from the group consisting of zinc oxide, aluminum oxide, sodium oxide, potassium oxide, cerium oxide, titanium oxide, zirconium oxide, yttrium oxide, barium oxide, lithium oxide, calcium oxide and calcium fluoride.

6. A dental restoration as in claim 1, further comprising an opaque porcelain layer, wherein said bond layer is disposed between said opaque layer and said coping, and said opaque layer is disposed between said bond layer and said body porcelain, said opaque layer comprising a first component mixture and a second component mixture, said first component mixture comprising 70–80 percent by weight of said opaque porcelain composition and consisting essentially of:

Component (A) 50–70 percent by weight silicon dioxide,
Component (B) 7–33 percent by weight boron oxide,
Component (C) at least 8 percent by weight zinc oxide,
Component (D) up to 4 percent by weight aluminum oxide,
Component (E) up to 4 percent by weight titanium oxide,
Component (F) up to 12 percent by weight sodium oxide,
Component (G) up to 8 percent by weight potassium oxide,
Component (H) up to 3 percent by weight cerium oxide,
Component (I) up to 1 percent by weight zirconium oxide, and
Component (J) up to 1 percent by weight of a complex of yttrium oxide and cerium oxide, said second component mixture comprising 20-30 percent by weight of said opaque porcelain composition and consisting essentially of:

Component (K) up to 100 percent by weight titanium dioxide,
Component (L) up to 100 percent by weight cerium oxide,
Component (M) up to 100 percent by weight stannous oxide, and
Component (N) up to 100 percent by weight zinc oxide.

7. A dental restoration as in claim 2, wherein said bond layer further comprises from about 4 to about 7% by weight of at least one member selected from the group consisting of sodium oxide, potassium oxide and lithium oxide.

8. A dental restoration as in claim 7, wherein said bond layer further comprises up to 5% by weight calcium fluoride.

9. A dental restoration as in claim 7, wherein said bond layer comprises titanium dioxide in an amount between about 40 to 50 percent by weight, boron oxide in an amount between about 8 and about 16 percent by weight, silicon dioxide in an amount of between about 8 and about 16 percent by weight and a fluoride selected from the group consisting of alkali and alkaline earth metal fluorides.

* * * * *